United States Patent [19]

Gonzalez et al.

[11] Patent Number: 4,716,115
[45] Date of Patent: Dec. 29, 1987

[54] DERIVED NISIN PRODUCING MICROORGANISMS, METHOD OF PRODUCTION AND USE AND PRODUCTS OBTAINED THEREBY

[75] Inventors: Carlos F. Gonzalez; Alfred J. Gryczka, both of Sarasota, Fla.

[73] Assignee: Microlife Technics, Inc., Sarasota, Fla.

[21] Appl. No.: 884,890

[22] Filed: Jul. 11, 1986

Related U.S. Application Data

[63] Continuation of Ser. No. 529,614, Sep. 6, 1983, abandoned.

[51] Int. Cl.$^4$ .................. C12N 15/00; C12N 1/20; C12P 21/00; C12P 21/04
[52] U.S. Cl. ............................. 435/172.3; 435/68; 435/71; 435/172.1; 435/253; 435/885; 435/320; 536/27
[58] Field of Search ............... 435/68, 172.3, 253, 435/317, 885, 71; 536/27

[56] References Cited

PUBLICATIONS

Lipinska et al, "Selection of Phage-Resistant Nisin-Producing Streptococci", Chem. Abstr. 87:165968f (1977).
Fuchs et al., "Possible Plasmid Nature of the Determinant for Production of the Antibiotic Nisin in Some Strains of *Streptococcus lactis*", J. Gen. Microbiol. 88:189 (1975).
Clewell, "Plasmids, Drug Resistance, and Gene Transfer in the Genus Streptococcus", Microbiological Reviews 45:409 (1981).
McClintock et al., J. Dairy Research 19:187 (1952) (incomplete English translation).
Gasson 1984 "Transfer of Sucrose Fermenting Ability, Nisin Resistance and Nisin Production into *Strepococcus lactis* 127", FEMS Lett., v. 21, 7-10.
Reddy et al., J. Food Science 40, 314–318 (1975).
Tramer, J., et al., J. Sci Fd. Agriculture 15, 522–528 (1964).
Campbell, L. L. et al., Food Tech 13:462–464 (1959).
Hurst, J. Gen. Microbiology 44:209–220 (1966).
Mattick and Hirsch 12th Intern. Dairy Congress 2 (Sect 3), 546–550 (1949).
Campbell et al., Food Preservation by Use of Chemicals 110–119.
Rayman, Applied and Environmental Tech 41:375–380 (1981).
Scott et al., Journal of Food Science 46:115–120 and 126 (1981).
Geis A. et al., Applied Environmental Microbiology 45:205–211 (1983).
Kozak et al., J. of Gen. Microbiology 83:295–302 (1974).
Park, et al., J. Bacteriology 149, 420–425 (1982).
McKay, L. et al Applied and Environmental Microbiology 40:84–91 (1980).
Scherwitz, K., et al., Applied and Environmental Microbiology 45:1506–1512 (1983).
LeBlanc, D., et al., J. of Bacteriology 137:878–884 (1979).
Terzaghi and Sandine Appl. Microbiol. 29:807–813 (1975).
LeBlanc, D., et al. J. in Plasmids and Transposons, edited by Colin Stuttard and Kenneth R. Rozee, Academic Press, 31–41 (1980).
Hurst, A., Advances Applied Microbiology 27:85–123 (1981).
Gonzalez, Carlos F., and Blair S. Kunka. Appl. Environ. Microbiol. 46:81–89 (1983).
Merck Index (8th Edition), p. 6375 (1983).
Gross and Morrell, National Institute of Health in Chem. and Eng. News, p. 18 (Sep. 24, 1973).
Reddy et al., J. of Food Science 35, 787–791 (1970).

*Primary Examiner*—James Martinell
*Attorney, Agent, or Firm*—Ian C. McLeod

[57] ABSTRACT

Derived microorganisms containing foreign DNA encoding for nisin production and a method for producing the derived microorganisms by transferring DNA to a recipient microorganism are described. The recipient microorganisms are preferably bacteria lacking in the ability to produce nisin. Nisin inhibits the growth of spoilage bacteria and is used in various materials for preservation, including foods and particularly at refrigeration temperatures. Nisin is also used in animals for improving the health of the animal. The foreign DNA is obtained from a donor microorganism and encodes for nisin production when transferred to the recipient microorganism.

18 Claims, No Drawings

DERIVED NISIN PRODUCING MICROORGANISMS, METHOD OF PRODUCTION AND USE AND PRODUCTS OBTAINED THEREBY

CROSS-REFERENCE TO RELATED APPLICATION

This application is a continuation of application Ser. No. 529,614, filed Sept. 6, 1983, now abandoned.

BACKGROUND OF THE INVENTION (1) Field of the Invention

The present invention relates to novel derived microorganisms and to a method for producing the derived microorganisms which contain foreign DNA encoding for nisin production. In particular, the present invention relates to derived bacteria containing foreign DNA encoding for nisin production.

(2) Prior Art

Nisin

The Merck Index (8th Edition) at page 6375 generally characterizes nisin as a polypeptide antibiotic produced by Streptococcus lactis, citing various publications including Mattick, Hirsch, Nature 154, 551 (1944); Lancet 250, 417 (1946); and 253, 5 (1947); Berridge et al., Biochem. J. 52, 529 (1952); and U.S. Pat. No. 2,935,503 (1960). The chemical structure is indicated to contain 34 amino acid residues, eight of which are rarely found in nature, including lanthionine (two alanines bonded to sulfur at the beta-carbons) and beta-methyllanthionine as described by Gross, J. Am. Chem. Soc. 93, 4634 (1971). Nisin is indicated to form crystals from ethanol and to be soluble in dilute acids. It is stable to boiling in acid solution. The Merck Index indicates that nisin is used in food processing and as a preservative, especially for cheese and canned fruits and vegetables.

A chemical structure of one form of nisin has been described by Gross and Morrell of the National Institute of Health in Chem. and Eng. News Page 18 (Sept. 24, 1973). The structure includes alpha-beta unsaturation in amino acids near the terminal amino and acid groups. It is speculated that the activity of nisin is related to reaction of the unsaturated amino acids with the sulfhydryl groups of enzymes in the affected microorganisms. Nisin generally has a published molecular weight range between about 6800 and 7500. Nisin is classed as an antibiotic produced by N-group lactic acid producing Streptococci. The inventors prefer the phrase "inhibitory substance" to "antibiotic" where nisin is generated in situ in a food by the microorganism, particularly by bacteria.

Use in Foods

Nisin in foods inhibits clostridial spoilage which is a major problem resulting from food storage. In addition, nisin inhibits psychotrophic bacteria which are particularly a problem with refrigerated foods. Thus nisin inhibits Streptococci of Groups A, B, E, F, H, K, M and N, Staphylococci, Micrococcus, Bacillus (some species) Clostridium, Mycobacterium, Lactobacillus, Octinomyces and Erysipelothrix. Nisin is particularly effective where the food has been partially heat treated. It is not affected by the presence of foods containing blood serum or milk. It is thus useful in settings where these substances are present in substantial amounts. At this time nisin can not be added to foods in the United States but is used in many countries elsewhere in the world; however, approval is being sought in the United States. It should be noted that nisin occurs naturally in fermented food products where nisin producing strains of Streptococcus lactis are present, particularly in milk products. Use in foods is described by Reddy et al J. of Food Science 35, 787–791 (1970) and in Reddy et al J. Food Science 40, 314–318 (1975). An assay procedure in foods is described by Trainer, J., et al J. Sci Fd. Agriculture 15 522–528 (1964). The Assay of Nisin In Foods. Fowler, G. G.; Garvis, B.; Tramer, J., Aplin & Barret Ltd., Yeovil, Somerset, U.K. Technical Series. Society for Applied Bacteriology, 1975, No. 8 pp 91–105.

Strains

Various strains of Streptococcus lactis are known to produce nisin, but S. cremoris and S. lactis subspecies diacetilactis do not. Such strains are described in: McClintok, H. et al. J. Dairy Research 19, 187–193 (1952); Campbell, L. L. et al Food Tech 13: 462–464 (1959); Hurst J. Gen Microbiology 44: 209–220 (1966); Mattick and Hirsch 12th Intern. Dairy Congress 2 (Sect 3) 546–540 (1949); Campbell et al, Food Preservation by Use of Chemicals 110–119 (about 1960); McClintock et al, J. Dairy Res 19: 187–193 (1952) (French); Rayman, Applied and Environmental Tech 41: 375, 380 (1981); Scott et al Journal of Food Science 40: 115–126 (1981); and in U.S. Pat. Nos. 2,935,503; 3,093,551; 2,785,108; and 3,295,989.

Various technical articles have appeared describing nisin producing Streptococcus lactis strains. Included are Geis A, et al Applied Environmental Microbiology 45: 205–211 (1983); Kozak et al J. of Gen. Microbiology 83: 295–302 (1974); Pack, et al, J. Bacteriology 149 420–425 (1982); McKay, L. et al Applied and Environmental Microbiology 40: 84–91 (1980); Hurst A, J. Gen Microbiology 44: 209–220 (1966); Scherwitz, K., et al., Applied and Environmental Microbiology 45: 1506–1512 (1983); LeBlanc, D., et al., J. of Bacteriology 137: 878–884 (1979) and LeBlanc D., et al in Plasmids and Transposons. Environmental Effects and Maintenance Mechanisms, Edited by Colin Stuttard and Kenneth R. Rozee, Academic Press, 31–41 (1980). Some of these publications describe the plasmids in Streptococcus lactis and in particular a 28 Mdal plasmid which may encode for nisin production; however, none of the publications describe the transfer of the nisin encoding plasmid to non-nisin producing recipient bacteria or to other microorganisms.

A summary regarding nisin appears in Hurst, A., Advances Applied Microbiology 27: 85–123 (1981). This publication describes what is generally known about nisin.

A major problem described in the prior art is the phage susceptibility of nisin producing strains of Streptococcus lactis. Another problem is that the nisin is expressed at relatively low levels in the naturally occurring strains of Streptococcus lactis and the strains are difficult to grow. Still another problem is that nisin alone has some limitations of inhibitory activity against food spoilage microorganisms.

Objects

It is therefore an object of the present invention to provide nisin producing derived microorganisms containing foreign DNA which encodes for nisin production. It is further an object of the present invention to provide a large collection of nisin producing derived microorganisms which have unrelated phage susceptibilities and which generate relatively large amounts of nisin. Also, provided are nisin producing derived microorganisms which can be adapted to become phage insensitive derivatives by direct challenge with phage for selection of insensitive clones without loss of desired functional characteristics, particularly nisin production. Further still it is an object of the present invention to provide nisin producing derived microorganisms which can be combined with other inhibitory substance producing microorganisms. These and other objects will become increasingly apparent by reference to the following description.

General Description

The present invention broadly relates to a novel nisin producing derived microorganism which contains foreign DNA, either chromosomal or extrachromosomal, which encodes for nisin production, which foreign DNA was obtained from a nisin producing donor microorganism and which foreign DNA was transferred to a recipient microorganism resulting in the nisin producing and usually nisin resistant derived microorganism. The present invention particularly relates to a novel nisin producing derived microorganism selected from a derived bacterium, yeast or fungus.

The following definitions are used herein:

(1) the phrase "donor microorganism" means a parental strain containing transferable DNA which encodes for nisin production, preferably strains of *Streptococcus lactis* bacteria which naturally produce nisin.

(2) The phrase "recipient microorganism" means a parental strain which does not naturally produce nisin or which produces relatively low amounts of nisin, preferably a bacterium, and may or may not be sensitive to (inhibited by) nisin.

(3) The phrase "derived microorganism" means nisin producing strains that result from introducing foreign DNA into a recipient microorganism, preferably from mating a donor microorganism which is nisin producing with a recipient microorganism which is non-nisin producing or low nisin producing to increase nisin production, and preferably a bacteria.

(4) The phrase "foreign DNA" means DNA which does not naturally occur in the recipient bacterium. The foreign DNA is introduced into the recipient bacterium by the method of the present invention.

(5) The phrase "inhibitory substance" means an antimicrobial agent including nisin produced by a microorganism which prevents the growth of other microorganisms.

The present invention particularly relates to a nisin producing derived bacterium selected from Streptococcus species, Pediococcus species, Lactobacillus species, Propionibacterium species, Micrococcus species, Leuconostoc species, Staphylococcus species, Clostridium species Flavobacterium species, Brevibacterium species, *E. coli* and Pseudomonas species.

The present invention further relates to a nisin producing derived yeast selected from Saccharomyces species, especially *S. cerevisiae;* Debaryomuces species, especially *D. hansenii;* Torulopsis species; Bretanomyces species; Candida species; Cryptococcus species; Kloeckera species; Kluyveromyces species and Schizosaccharomyces species.

The present invention finally relates to the nisin producing derived fungus selected from Penicillium species, Mucor species, Rhizopus species, Aspergillus species, Deuteromycetes species, Ascomycetes species, Geotrichum species and Monascus species.

The foreign DNA can be transferred to a recipient microorganism by transformation in the manner described in U.S. Pat. No. 4,237,224 to Cohen and Boyer and related patents using splicing of the nisin encoding DNA in a cloning vector. The cloning vectors described in U.S. Pat. No. 4,374,200 to Ronald H. Olsen and similar patents are useful. More conventional conjugal mating of donor and recipient microorganisms, which is preferred, can be used for the transfer. Transduction of the nisin encoding DNA dusing a virus (phage) is also possible.

The present invention also relates to the method for engineering a nisin producing derived microorganism which comprises transferring DNA, which encodes for nisin production in a donor microorganism, to a recipient microorganism, to result in a nisin producing derived microorganism, wherein the DNA is foreign to the recipient microorganism and encodes for nisin production in the derived microorganism; and isolating the nisin producing derived microorganism with the foreign DNA.

The present invention also relates to a nisin containing product elaborated by the nisin producing microorganism with the foreign DNA. The nisin containing product can contain in addition other inhibitory substances preferably those simultaneously elaborated by the nisin producing derived microorganism. The present invention includes a mixture of nisin, as a pure chemical or a crude nisin containing extract, mixed with a non-nisin producing *Streptococcus lactis* subspecies *diacetilactis* or a nisin producing derived microorganism which has been selected for resistance to nisin.

The present invention further relates to two or more of the nisin producing derived microorganism strains containing the foreign DNA as a mixture, which strains have different phage susceptibilities so as to enable the production of nisin without stringent anti-bacteriophage precautions. The strains can be packaged mixed or separately.

Finally the present invention relates to the method for treating animals which comprises feeding the animal the nisin producing microorganism which contains the foreign DNA, alone or in admixture with other microorganisms.

The present invention is based upon the fact that DNA encoding for nisin production in a donor microorganism can be incorporated into a recipient microorganism as foreign DNA to provide a new nisin producing derived microorganism. The resulting nisin producing derived microorganism is able to preserve foods and other materials and to provide inhibitory substances in animals, particularly birds and mammals, to maintain or improve their health. The nisin producing derived microorganisms containing the foreign DNA can be combined with non-nisin producing, nisin insensitive bacteria or other microorganisms preferably those which can produce other inhibitory substances structurally different from nisin.

Sometimes nisin can be encoded for in the naturally occurring nisin producing *Streptococcus lactis* by a plasmid. Also the plasmid DNA encoding for nisin can be incorporated into the chromosome of the recipient bacterium by natural ligation processes, which makes the removal of the characteristic in the derived microorganism difficult. Thus, in the present invention, the foreign DNA after transfer can be chromosomal or extrachromosomal in the derived microorganism.

DNA encoding for nisin can be separated from the natural nisin producing *Streptococcus lactis* in the form of a cleaved fragment or plasmid. This may be accomplished by redigestion of the nisin encoding DNA. The fragment can then be cloned into a suitable cloning vector and transferred with an introduced DNA into a recipient microorganism. The introduced foreign DNA can also be transferred by transduction of the chromosomal DNA or plasmid DNA using a virus. The plasmid can also be transferred by conjugal mating of related or unrelated genus and species. The term "transfer" is used herein in its broadest sense to designate any means for placing the DNA encoding for nisin production into a recipient microorganism as foreign DNA. The resulting nisin producing derived microorganism may have multiple copies of the foreign DNA in each cell which can greatly increase the amount of nisin produced per cell subject to cellular limitations as to concentration of nisin.

As is known in the art, the derived microorganisms are provided in various preserved forms which increase viability during storage and shipment. Such forms include: liquid non-concentrated or concentrated cultures, frozen or non-frozen cultures and stabilized dried or lyophilized cultures. The cultures usually contain biologically pure forms of the derived microorganisms. Amounts of the microorganism at least about $10^6$ cells per gram, and preferably at least about $1 \times 10^9$ cells per gram in preserved form are preferred. Generally, concentrations at least about $10^9$ cells per gram require means for removal of liquid growth medium from the cells usually by centrifugation or reverse osmosis. Various stabilizing agents such as glycerol, milk powder and the like are used for freezing and lyophilization. The derived microorganism cells are usually grown in a growth medium including a source of carbon, nitrogen and essential minerals. All of this is well known to those skilled in the art as can be seen from the large body of patent art.

SPECIFIC DESCRIPTION

The present invention particularly relates to a biologically pure nisin and lactic acid producing derived bacterium which is not sensitive to nisin and containing plasmid derived DNA, encoding for nisin production from a donor nisin producing *Streptococcus lactis* wherein the DNA has been transferred to a nisin sensitive recipient bacterium resulting in the nisin and lactic acid producing derived bacterium. The recipient bacterium is preferably *Streptococcus lactis* subspecies *diacetilactis*. The donor bacterium for *S. lactis* is preferably *Streptococcus lactis* ATCC 11,454 which transfers the nisin trait only to isogenic strains as can be seen from Table 1. Sucrose utilization also is transferred with the nisin trait. A related known nisin producing strain is NRRL-B-15,470 (NIRD 1404) which could be used. The derived donors are *S. lactis*, NRRL-B-15,459 and NRRL-B-15,460 which can transfer the nisin, sucrose trait intergenetically. All of the nisin producing derived microorganisms which are transconjugants can potentially be used as donors of the nisin trait. The reason may be that the plasmid encoding for nisin and sucrose may have been modified in the primary transfer. The intergenetic recipient bacterium is preferably *Streptococcus lactis* subspecies *diacetilactis* NRRL-B-15,005, NRRL-B-15,006, NRRL-B-15,018, NRRL-B-12,070 (DRC3, cit−, lac+), and NRRL-B-12071 (DRC3, lac+, cit−), and *S. lactis* NRRL-B-15,454, NRRL-B-15,452, NRRL-B-15,455, NRRL-B-15,456, NRRL-B-15,457. The resultant nisin producing derived bacterium with the foreign DNA is preferably selected from *Streptococcus lactis* subspecies *diacetilactis* NRRL-B-15,464, (and related transconjugants from similar matings 15,465, 15,466 and 15,467), 15,468 and 15,469 and isogenic bacterial derivatives thereof as described more fully hereinafter with the appropriate antibiotic resistance marker(s) removed by selection.

The present invention particularly relates to a biologically pure nisin and lactic acid producing bacterium which is not sensitive to nisin and which is derived by conjugal mating of a nisin producing *Streptococcus lactis* donor bacterium containing a plasmid, which codes for the nisin production in the donor bacterium, with a non-nisin producing and nisin sensitive lactic acid producing recipient bacterium. The conjugal mating results in the nisin and lactic acid producing derived bacterium wherein, in some instances, the original plasmid from the donor encoding for nisin production can not be removed as a plasmid from the nisin and lactic acid producing derived bacterium because of recombination with the host chromosome of the recipient bacterium. The recipient bacterium can be inhibited by nisin prior to the transfer. The plasmid which encodes for nisin production (and sucrose fermentation) from the donor bacterium preferably measures about 29 Mdal in length and may exist as 29 or altered form i.e. reduced or enlarged or recombined with host chromosome DNA in the derived bacterium.

The present invention particularly relates to the method for producing a nisin and lactic acid producing derived bacterium which is not sensitive to nisin and which comprises: conjugally mating a nisin producing *Streptococcus lactis* donor bacterium containing a plasmid which codes for the nisin production in the donor bacterium with a non-nisin producing and nisin sensitive lactic acid producing recipient bacterium, and isolating the nisin and lactic acid producing derived bacterium produced by the mating.

Further, the present invention relates to an improvement in a method of preserving a material such as a food by incorporating a lactic acid producing derived bacterium into the material which comprises incorporating in the material a nisin and lactic acid producing derived bacterium which is not sensitive to nisin and containing DNA derived from a plasmid which codes for nisin production from a nisin producing donor *Streptococcus lactis* and which has been transferred to a nisin sensitive recipient bacterium to produce the nisin and lactic acid producing derived bacterium. The foreign DNA encodes for nisin production and is either integrated into the chromosome or extrachromosomal in the nisin producing derived bacterium. The materials can include all sorts of microbially degradable products for agricultural, industrial, food and other uses including silage, cutting oil and foods. The foods include fresh meat, comminuted, fermented and non-fermented meat; fresh chicken, fish, milk and other dairy products, commercially prepared salads, vegetables, dressings, sauces and other foods subject to spoilage during refrigerated storage.

Also, the present invention particularly relates to an improved preserved material produced by incorporating into the material a lactic acid producing derived bacterium or a product produced by the derived bacterium, which comprises (1) a material containing a nisin and lactic acid producing derived bacterium, which is not sensitive to nisin and containing DNA derived from a plasmid which encodes for nisin production from a nisin producing *Streptococcus lactis* donor bacterium which has been transferred to a nisin sensitive recipient bacterium to produce the nisin and lactic acid derived bacterium or (2) incorporating in the material a nisin containing product of such derived bacterium or (3) incorporating in the material a nisin containing product of such derived bacterium along with a microorganism which produces other inhibitory substance(s) but does not produce nisin or (4) incorporating in the material a nisin containing product of such derived bacterium along with a microorganism which produces other inhibitory substances in addition to nisin.

Finally the present invention particularly relates to a nisin containing product produced by the derived bacterium previously described containing in addition an inhibitory substance from *Streptococcus lactis* subspecies *diacetilacits*.

DETAILED DESCRIPTION

EXAMPLE 1

In order to determine if sucrose utilization and nisin production could be transferred by conjugation, *S. lactis* ATCC-11454 (utilizes sucrose and produces nisin) was used as the donor strain in a mating experiment where *S. lactis* subsp. *diacetilactis* and *S. lactis* (neither strain utilizes sucrose and neither strain produce nisin) were the recipient strains. The mating conditions were as described by Gonzalez and Kunka, (Gonzalez, Carlos F., and Blair S. Kunka. Appl. Environ. Microbiol. 46: 128-132 (1983)) except that the mating filters were not overlayed with agar. Instead, the filter with the cells facing the agar surface were placed in a BBL ™ -Anaerobic Jar with $CO_2/H_2$ atmosphere for 3 to 4 hours. Transconjugants were selected for the chromosomal resistance of the recipient and ability to utilize sucrose or resistance to nisin (1000 units/ml).

An isogenic strain of *S. lactis* ATCC 11,454 was constructed. Strain *S. lactis* ATCC-11,454 (utilizes lactose and sucrose, and produces nisin) was temperature cured of a resident 29 Mdal plasmid by exposure to an elevated growth temperature (40° C.). This cured strain utilized lactose but did not utilize sucrose and did not produce nisin. Subsequently, this strain was subjected to an additional heat curing at 40° C. to remove an additional resident 32 Mdal plasmid to result in constructed strain *S. lactis* ATCC 11,454, which was lactose negative (Lac−), sucrose negative (Suc−) and did not produce nisin (Nis−). This constructed strain was designated as *S. lactis* NRRL-B-15,453 (Lac−, Suc−, Nis−). NRRL-B-15,453, then was exposed to increasing concentrations of streptomycin to obtain a chromosomal mutation for the antibiotic at a concentration of 1000 g/ml. This NRRL-B-15,453 Sm$^r$ (streptomycin resistant) strain was designated as NRRL-B-15,454. Strain NRRL-B-15,454 was then used as a recipient in the conjugal mating experiments.

Table 1 describes the experiments and the results. In these experiments, transfer of sucrose utilization and nisin production only was observed with the isogenic recipient *S. lactis* NRRL-B-15,454. Transfer of sucrose utilization and nisin production intragenerically from *S. lactis* NRRL-B-15,454 to *S. lactis* NRRL-B-15,452 and *S. lactis* subsp. *diacetilactis* NRRL-B-15,006-Sm$^r$ was not observed.

TABLE 1

| Intraspecies Conjugal Matings | | |
|---|---|---|
| Donor | Recipients | Transfer frequencies per donor |
| *S. lactis* ATCC 11454 | *S. lactis* NRRL-B-15452 | NO |
| " | *S. lactis* NRRL-B-15454 | $1 \times 10^{-5}$ |
| " | *S. lactis* subsp. *diacetilactis* NRRL-B-15006-Sm$^r$ | NO |

NO - Not Detected
Sm$^r$ - Resistance to streptomycin at concentration of 1000 μg/ml.

Mating conditions as described by Gonzalez and Kunka, 1983 (Appl. Environ. Microbiol. 46: 81-89). See Example 1 in text for exception.

Transfer frequency is expressed as the number of nisin resistant and nisin producing colonies per donor colony forming units (CFU). Donor CFU were determined before mating. Transconjugants were selected for the chromosomal resistance of the recipient and ability to utilize sucrose or resistance to nisin (1000 units/ml).

EXAMPLE 2

*S. lactis* ATCC 11,454 was exposed to increasing concentrations of rifamycin to obtain a rifamycin resistant (Rif$^r$) mutant (resistant to 400 μg/ml). The mutant was used as a recipient in a conjugal mating experiment with a *S. sanguis* V683 strain which contains the conjugative plasmid pIP501. The resultant transconjugant (*S. lactis* ATCC 11,454 Rif$^r$ (pIP501)) was isolated and was designated as *S. lactis* NRRL-B-15,458. *S. lactis* NRRL-B-15,458 along with *S. lactis* ATCC 11,454 were used as donors in isogenic and intrageneric matings to determine conjugal transfer of the nisin genes. The mating conditions for the experiments were as described in Example 1 above.

Table 2 describes results of matings in which strain *S. lactis* NRRL-B-15,458 was used as a donor and *S. lactis* NRRL-B-15,452, *S. lactis* NRRL-B-15,454 (an isogenic strain of *S. lactis* ATCC 11,454) and *S. lactis* subsp. diacetilactis NRRL-B-15,006-Sm$^r$ were used as recipients. Transer of plasmid pIP501 was observed to occur in two *S. lactis* strains, while no transfer was detected to *S. lactis* subsp. *diacetilactis*. Transfer of sucrose utilization and nisin production was observed only to isogenic strain *S. lactis* NRRL-B-15,454 and was at a frequency of $1.4 \times 10^{-3}$.

TABLE 2

| Conjugal Transfer of Nisin Genes | | | |
|---|---|---|---|
| | | Transfer frequency per donor | |
| Donor | Recipient | pIP501 | Nisin |
| *S. lactis* NRRL-B-15458 | *S. lactis* NRRL-B-15452 | $2 \times 10^2$ | NO |
| *S. lactis* NRRL-B-15458 | *S. lactis* NRRL-B-15454 (isogenic strain) | $2.7 \times 10^{-5}$ | $1.4 \times 10^{-3}$ |
| *S. lactis* NRRL-B-15458 | *S. lactis* subsp. *diacetilactis* NRRL-B-15006-Sm$^r$ | NO | NO |

NO - Not Detected
Mating conditions as described in Example 1

When *S. lactis* NRRL-B-15,458 was mated with *S. lactis* NRRL-B-15,454 (isogenic strain) two different phenotypes of transconjugants were obtained. One phenotype was lactose negative, sucrose positive and produced nisin. This isolate was designated as *S. lactis* NRRL-B-15,459. The other transconjugant was lactose negative, sucrose positive, produced nisin and contained plasmid pIP501. This isolate was designated as *S. lactis* NRRRL-B-15,460.

These derived strains, unlike the donor strain, were streptomycin resistant, rifamycin sensitive and did not produce acid from lactose. However, unlike the recipient parental strain the derived strains were now nisin producers and were able to utilize sucrose as a source of carbon to produce acid. Therefore, only isogenic transfer of the sucrose utilizing nisin producing trait was observed by strains *S. lactis* ATCC 11,454 and its pIP501 derivative *S. lactis* NRRL-B-15,458.

EXAMPLE 3

*S. lactis* NRRL-B-15,459 was tested for ability to transfer nisin production to *S. lactis* NRRL-B-15,452. Recipient strain NRRL-B-15,452 was negative for production of nisin, sensitive to nisin and unable to utilize sucrose as a source of carbon to produce acid. The mating conditions were as described in Example 1 and results are described in Table 3.

TABLE 3

| Intrageneric Transfer of Nisin and Sucrose Utilization Genes | | |
|---|---|---|
| Donor | Recipient | $Nis^+, Suc^+$ Transconjugants per donor |
| *S. lactis* NRRL-B-15459 | *S. lactis* NRRL-B-15452 | $6 \times 10^{-5}$ |

Conditions as described in Table 1
$Suc^+$ = Sucrose positive; able to utilize sucrose to produce acid.
$Nis^+$ = Nisin positive; able to produce nisin.

*S. lactis* NRRL-B-15,459 was able to transfer nisin production, resistance and the ability to utilize sucrose to a non-isogenic strain of *S. lactis* NRRL-B-15,452.

EXAMPLE 4

*S. lactis* NRRL-B-15,460 was tested for ability to transfer nisin production to *S. lactis* NRRL-B-15,452, *S. lactis* subsp. *diacetilactis* NRRL-B-15,455 and NRRL-B-15,456. Recipient strains NRRL-B-15,452, NRRL-B-15,455 and NRRL-B-15,456 are negative for production of nisin, sensitive to nisin and unable to utilize sucrose as a source of carbon to produce acid.

The mating conditions were as described in Example 1 and the results are described in Table 4.

TABLE 4

| | Intrageneric Transfer of Nisin Genes and Sucrose Utilization Genes | | | | |
|---|---|---|---|---|---|
| | Recipient | | Transfer Frequency | Strain designation of representative | Transconjugant |
| Donor | Strain | Phenotype | per donor | transconjugant | Phenotype |
| *S. lactis* NRRL-B-15460 | *S. lactis* NRRL-B-15452 | $Suc^-, Nis^-$ | $3.5 \times 10^{-5}$ | NRRL-B-15461 (pIP501 neg.) | $Suc^+, Nis^+$ |
| *S. lactis* NRRL-B-15460 | *S. lactis* NRRL-B-15452 | $Suc^- Nis^-$ | — | NRRL-B-15462 (pIP501 pos.) | $Suc^+, Nis^+$ |
| *S. lactis* NRRL-B-15460 | *S. lactis* subsp. *diacetilactis* NRRL-B-15455 | $Suc^-, Nis^-$ | $2 \times 10^{-6}$ | NRRL-B-15464 | $Suc^+, Nis^+$ |
| *S. lactis* NRRL-B-15460 | *S. lactis* subsp. *diacetilactis* NRRL-B-15456 | $Suc^-, Nis^-$ | $2 \times 10^{-7}$ | NRRL-B-15469 | $Suc^+, Nis^+$ |
| *S. lactis* NRRL-B-15460 | *S. lactis* subsp. *diacetilactis* NRRL-B-15005-Fus$^r$ | $Suc^-, Nis^-$ | $1 \times 10^{-6}$ | NRRL-B-15005 Fus$^r$, Suc$^+$, Nis$^-$ | $Suc^+, Nis^+$ |

Conditions and selection as described in Table 1.
$Suc^+$ = Sucrose positive; able to utilize sucrose to produce acid.
$Nis^+$ = Nisin positive; able to produce nisin.
$Nis^-$ = Nisin negative; unable to produce nisin.
$Fus^r$ = Resistance to fusidic acid at concentration of 20 μg/ml
$Lac^-$ = Lactose negative. Not able to utilize lactose to produce acid.
neg. = negative
pos. = positive

*S. lactis* NRRL-B-15,460 was able to transfer nisin production, nisin resistance and ability to utilize sucrose to a non-isogenic strain of *S. lactis* NRRL-B-15452 and to *S. lactis* subsp. *diacetilactis* NRRL-B-15455.

Many transconjugant, derived strains were isolated from the conjugal matings described in Examples 3 and 4. Derived *S. lactis* NRRL-B-15461 is typical of a transconjugant of *S. lactis* NRRL-B-15452. Derived *S. lactis* subsp. *diacetilactis* NRRL-B-15469 is typical of a transconjugant of *S. lactis* subsp. *diacetilactis* NRRL-B-15456.

Table 5 summarizes phenotypic characteristics of transconjugant strains resulting from matings described in Example 4. Transconjugants obtained from each mating were analyzed for selected and unselected markers. Analysis of plasmid content of transconjugants confirmed them as recipient types. Additionally transconjugants were tested for sensitivity to their respective recipient homospecific phages. The transconjugants were lysed by their homospecific phages while donor controls showed no sensitivity.

TABLE 5

| Phenotypic characteristics of Parental Recipient Strain and Derived Strains of Table 4 Matings | | | | |
|---|---|---|---|---|
| | | Phenotypic Characteristics | | |
| Strain # | status | Nisin Production | Nisin Resistance | Sucrose Utilization |
| *S. lactis* NRRL-B-15452 | Parental Recipient | − | − | − |
| *S. lactis* NRRL-B-15461 | Derived | + | + | + |
| *S. lactis* subsp. *diacetilactis* | Parental Recipient | − | − | − |

TABLE 5-continued

Phenotypic characteristics of Parental Recipient
Strain and Derived Strains of Table 4 Matings

| Strain # | status | Nisin Production | Nisin Resistance | Sucrose Utilization |
|---|---|---|---|---|
| NRRL-B-15455 S. lactis subsp. diacetilactis | Derived | + | + | + |
| NRRL-B-15464 S. lactis subsp. diacetilactis | Parental Recipient | − | − | − |
| NRRL-B-15456 S. lactis subsp. diacetilactis | Derived | + | + | + |
| NRRL-B-15469 | | | | |

Nisin production - Assay (see text)
Nisin resistance - Growth on medium containing Nisaplin ™ at 1000 µg/ml.
Sucrose - utilization - medium BM containing sucrose at .5% (Gonzalez and Kunka Appl. and Environ. Microbiol. 46: 81–89, 1983).

EXAMPLE 5

*S. lactis* subsp. *diacetilactis* NRRL-B-15464, a transconjugant, derived strain from a first mating subsequently was used as a donor in an isogenic mating with *S. lactis* subsp. *diacetilactis* NRRL-B-15018 $Sm^r$ (Streptomycin resistant) and *S. lactis* subsp. *diacetilactis* NRRL-B-15005 $Fus^r$ (fusidic acid resistant).

Table 6 describes the results of the mating experiments. Transfer of sucrose utilization and nisin production traits were observed in the two isogenic recipient strains. Transconjugants from each mating were examined for their plasmid content. Additionally, analyses for non-selected traits were conducted. Transconjugants were confirmed as recipient types.

TABLE 6

Intraspecies Transfer of Sucrose Utilization and Nisin producing genes

| Donor | Recipient Strain | Phenotypes | Nisin Transfer Frequency | Strain designation of representative Transconjugant | Transconjugant Phenotype |
|---|---|---|---|---|---|
| S. lactis subsp. diacetilactis NRRL-B-15464 | S. lactis subsp. diacetilactis NRRL-B-15018-$Sm^r$ | $Suc^-,Nis^-$ | $1.77 \times 10^{-5}$ | S. lactis subsp. diacetilactis SLA3.18 | $Suc^+,Nis^+$ |
| S. lactis subsp. diacetilactis NRRL-B-15464 | S. lactis subsp. diacetilactis NRRL-B-15005-$Fus^r$ | $Suc^-,Nis^-$ | $4.5 \times 10^{-7}$ | S. lactis subsp. diacetilactis SLA3.42 | $Suc^+,Nis^+$ |

Conditions and selection as described in Table 1
$Suc^+$ = Sucrose positive; able to utilize sucrose to produce acid.
$Nis^+$ = Nisin positive; able to produce nisin.
$Nis^-$ = Nisin negative; unable to produce nisin.
$Sm^r$ = Resistance to streptomycin at concentration of 1000 µg/ml.
$Fus^r$ = Resistance to fusidic acid at concentration of 20 µg/ml.

EXAMPLE 6

Production of nisin by strain *S. lactis* subsp. *diacetilactis* NRRL-B-15464 in comminuted meat incubated at 10° C.

To determine production of nisin by individual colonies of test strains, the colonies were replicated in petri dishes containing peptonized milk agar which had previously been flooded with an 18 hour culture of *S. cremoris* ATCC 14365. Strain ATCC 14365 is a nisin sensitive strain used to assay nisin production (J. Gen. Microbiol. 4: 71, 1950). After 18 hours of incubation, the appearance of zones of inhibition is indicative of nisin production. The method is that of Kozak et al J. Gen. Microbiol. 83: 295–302 (1974).

The nisin content of meat was determined by "The Quantitative Agar Diffusion Assay used for the estimation and differentiation of nisin in food" as described by Fowler et al. (The Assay of Nisin in Foods. Fowler, G. G., Jarvis, B., Tramer, J. Aplin & Barret Ltd., Yeovil, Somerset, UK, Technical Series, Society for Applied Bacteriology, 1975, No. 8, pp. 91–105.

A standard curve was prepared by adding a known concentration of purified nisin to meat. The meat sample was then treated by the method of Tramer et al. The food extract was assayed by the agar diffusion method and a log nisin concentration vs. zone diameter size curve was plotted. *S. cremoris* ATCC 14365 was used as the indicator organism. Additionally, strain *S. lactis* ATCC 11454, a nisin producing and therefore nisin insensitive, also was used as an indicator organism.

Highly purified nisin (obtained from Aplin & Barrett, Ltd.) was added to meat samples and nisin concentrations were calculated using a standard curve.

The inoculum of test organism was prepared by growing NRRL-B-15464 in 500 ml M17 broth (Terzaghi and Sandine Appl. Microbiol. 29: 807 ∝ 813, 1975) for 18 hours. Cells were obtained and washed twice by centrifugation at 10,000 RPM at 10° C. for 10 minutes and resuspended in Standard Methods phosphate buffer (E. H. Marth, (Ed.) Standard Methods for Examination of Dairy Products, 14th ed. p. 62, Amer. Public Health Assoc. Washington, D.C. Cell suspension was adjusted spectophotometrically to approximately $1.5 \times 10^9$ colony forming units/ml. Actual number was determined to be $1.7 \times 10^9$ CFU/ml. A fresh picnic (pork) (skin or bone in) was purchased from a local meat supply company. The skin was asceptically removed and the meat comminuted in a sterilized meat chopper. The meat then was apportioned into 50 and 100 g quantities and placed in sterile containers. Containers were set up as follows:

A. Eleven containers with 100 g meat and glucose added to a final concentration of 0.5% by weight. For analysis, these samples were split into two aliquots. One aliquot was assayed without further treatment. The remaining aliquot was used to construct a standard curve by adding a known amount of purified nisin (100–200 units/g of meat).

B. Three containers with 50 g of meat glucose to a final concentration of 0.5% by weight of meat and 100 units of added nisin per gram of meat. This sample was assayed daily for nisin.

C. Eleven containers with 100 g of meat, glucose to a final concentration of 0.5% by weight of meat and strain *S. lactis* NRRL-B-15464 to a final concentration of $1.7 \times 10^7$ CFU/g of meat. Results are shown on Table 7.

TABLE 7

Production of Nisin by Derived strain *S. lactis* subsp. *diacetilactis* NRRL-B-15464 Inoculated into Comminuted meat which was incubated at 10° C.

| | Nisin Content Express As units per gram of meat | | | Organoleptic Evaluation | | |
|---|---|---|---|---|---|---|
| Day | Control Meat No Nesin No culture | Meat with Added Nisin | Meat with added NRRL-B-15464 | Control Meat No Nisin No culture | Meat with Added Nisin | Meat with added NRRL-B-15464 |
| 0  | 0 | 133 | 0   | 0  | 0  | 0 |
| 1  | 0 | ND  | 0   | ND | 0  | 0 |
| 2  | 0 | 23  | 0   | 0  | 0  | 0 |
| 3  | 0 | 5   | 29  | 1  | 0  | 0 |
| 4  | 0 | ND  | 156 | 3  | ND | 0 |
| 5  | 0 | ND  | 140 | 3  | ND | 0 |
| 6  | 0 | ND  | 115 | 3  | ND | 0 |
| 7  | 0 | ND  | 131 | 4  | ND | 0 |
| 8  | 0 | ND  | 65  | 4  | ND | 0 |
| 9  | 0 | ND  | 72  | 4  | ND | 0 |
| 10 | 0 | ND  | 42  | 4  | ND | 2 |

Sample assayed by agar diffusion method as described in text.
ND - not determined
Organoleptic scale =
0 - fresh, clean meat aroma, good red color
1 - slight off aroma, good red color
2 - slight off aroma, fair red color
3 - off aroma, poor red color
4 - putrid aroma, slimy appearance, no red color

EXAMPLE 7

Nisin content in milk was determined by the method used for meat described in Example 6.

The inoculum of test organisms were prepared by growing microorganisms in M17 broth for 18 hours. Cells were obtained and washed twice by centrifugation at 10,000 rpm at 10° C./10 minutes and resuspended in Standard Methods phosphate buffer pH7.2. Suspension was adjusted spectrophotometrically to $1.5 \times 10^8$ colony forming units/ml. Non-fat dry milk (10% w/v) was steamed for 30 minutes cooled and glucose added to a final concentration of 0.5% by weight of milk. Fifty ml of milk-glucose was inoculated at a rate of approximately $10^6$ CFU/ml and incubated at 32° C. Samples were assayed daily.

Nisin assay protocol: (1) 30 ml of sample was assayed (2) the pH was adjusted to 2 with 5N HCl (3) The sample was boiled for 5 minutes (4) Chilled (5) The sample was centrifuged 10,000 rpm for 10 minutes at 10° C. and (4) Supernatant was assayed by Quantitative Agar Diffusion Method (see above). The assay organism was ATCC 14365 which is sensitive to nisin. ATCC 11454 is insensitive to nisin and a nisin producing strain. A standard curve was constructed on a daily basis by adding nisin to a milk sample at 100 units/ml. The results are shown on Table 8.

TABLE 8

Production of Nisin by Parental and Derived Strains in Milk Incubated at 32° C.

| | | Units of Nisin Per ml of Milk | | | |
|---|---|---|---|---|---|
| Strain | Status | Day 0 | Day 1 | Day 2 | Day 3 |
| S. lactis NRRL-B-15455 | P | 0 | 0 | 0 | 0 |
| S. lactis subsp. diacetilactis NRRL-B-15464 | D | 0 | 39 | 54 | 122 |
| S. lactis ATCC 11454 | P | 0 | 45 | 128 | 109 |
| S. lactis NRRL-B-15452 | P | 0 | 0 | 0 | 0 |
| S. lactis NRRL-B-15461 | D | 0 | 10.5 | 49.3 | 44.8 |
| S. lactis subsp. diacetilactis NRRL-B-15456 | P | 0 | 0 | 0 | 0 |
| S. lactis subsp. diacetilactis NRRL-B-15469 | D | 0 | 30 | 182 | 209 |

* = units/ml
P = parental
D = Derived
Strains NRRL-B-15455, NRRL-B-15452, and NRRL-B-15456 represent parental type strains and strains NRRL-B-15464, NRRL-B-15461 and NRRL-B-15469 represent their derived strains respectively.
Assay as described in text.

The derived microorganisms, particularly the derived bacteria, can produce nisin (and possibly other substances which inhibit microorganisms) at refrigeration temperatures which is a distinct advantage in the preservation of foods. This is shown by the results in Table 7 where control meat without a derived microorganism started to spoil at day 3 and became putrid by day 7 as compared to meat with a derived microorganism which did not even start to spoil until day 10.

The preferred *Streptococcus lactis* subspecies *diacetilactis* is NRRL-B-15469 with the fusidic acid resistance marker removed by selection and *S. lactis* subspecies *diacetilactis* NRRL-B-15464 with the rifamycin resistance marker removed by selection. Neither of these derived strains are capable of utilizing lactose.

The reference to "NRRL" herein is to the National Regional Research Laboratory in Peoria, Ill. The designated strains are freely available to those requesting them by reference to the strain name and number.

We claim:

1. A nisin producing engineered bacterium of the genus Streptococcus which contains foreign DNA which encodes for nisin production, which foreign DNA was obtained from a nisin producing donor bacterium and which foreign DNA was transferred to a recipient bacterium resulting in the nisin producing engineered bacterium, wherein the donor bacterium is a naturally occurring Streptococcus species containing plasmid DNA from a 29 Mdal plasmid encoding for sucrose utilization and nisin production and nisin resistance and wherein the recipient bacterium is a Streptococcus species which is sensitive to nisin and which does not naturally produce nisin.

2. The nisin producing engineered bacterium of claim 1 wherein the donor bacterium from which the plasmid DNA has been transferred is a nisin producing *Streptococcus lactis* strain.

3. The nisin producing engineered bacterium of claim 1 wherein the donor bacterium from which the plasmid DNA has been transferred is *Streptococcus lactis* and the recipient microorganism is *Streptococcus lactis* subspecies *diacetilactis*.

4. The nisin producing engineered bacterium of claim 1 wherein the donor from which the plasmid DNA has been transferred is selected from the group consisting of *Streptococcus lactis* ATCC 11,454, NRRL-B-15,458, NRRL-B-15,459, NRRL-B-15,460, NRRL-B-15,461, NRRL-B-15462 and NRRL-B-15470.

5. The nisin producing engineered bacterium of claim 1 wherein the recipient is selected from the group consisting of *Streptococcus lactis* subspecies *diacetilactis* NRRL-B-15005, NRRL-B-15006, NRRL-B-15018, NRRL-B-12070 and NRRL-B-12071.

6. The nisin producing engineered bacterium of claim 1 wherein the recipient bacterium to which the plasmid DNA has been transferred produces compounds inhibitory against Gram-negative bacteria, and in particular psychotrophic bacteria, and the donor bacterium from which the plasmid DNA has been transferred produces nisin so that nisin and the compounds inhibitory against the Gram-negative bacteria are both expressed by the engineered nisin producing bacterium.

7. The nisin producing engineered bacterium of claim 6 which is inhibitory against Gram-positive bacteria and in particular spore-forming Gram-positive bacteria and also is inhibitory against Gram-negative bacteria and in particular psychotrophic Gram-negative bacteria.

8. The nisin producing engineered bacterium of claim 1 selected from the group consisting of *Streptococcus lactis* subspecies *diacetilactis* NRRL-B-15464, NRRL-B-15,465, NRRL-B-15,466, NRRL-B-15,467, NRRL-B-15,468 and NRRL-B-15,469.

9. The nisin producing engineered bacterium of claim 1 mixed with non-nisin producing *Streptococcus lactis* subspecies *diacetilactis* which has been selected for resistance to nisin and production of an inhibitory substance which is inhibitory to Gram-negative bacteria.

10. The engineered bacterium of claim 1 which is phage resistant.

11. The method for engineering a nisin producing bacterium of the genus Streptococcus which comprises:

(a) transferring plasmid DNA which encodes for nisin production in a donor bacterium to a recipient bacterium to produce a nisin producing engineered bacterium, wherein the plasmid DNA is foreign to the recipient bacterium and encodes for nisin production and nisin resistance in the recipient bacterium wherein the donor bacteria is a Streptococcus species containing plasmid DNA derived from a 29 Mdal plasmid encoding for sucrose utilization, nisin production and nisin resistance and wherein the recipient bacterium is a Streptococcus species which is sensitive to nisin and does not naturally produce nisin; and (b) isolating the nisin producing engineered bacterium.

12. The method of claim 11 wherein the donor bacterium is selected from the group consisting of *Streptococcus lactis* ATCC 11,454, NRRL-B-15,458, NRRL-B-15,459, NRRL-B-15,460, NRRL-B-15,461, NRRL-B-15,462, NRRL-B-15,470.

13. The method of claim 11 wherein the recipient bacterium is selected from the group consisting of *Streptococcus lactis* subspecies *diacetilactis* NRRL-B-15005, NRRL-B-15006, NRRL-B-15018, NRRL-B-12070, NRRL-B-12071.

14. The method of claim 11 wherein the engineered bacterium is a transconjugant selected from the group consisting of *Streptococcus lactis* subspecies *diacetilactis* NRRL-B-15464, NRRL-B-15,465, NRRL-B-15,466, NRRL-B-15,467, NRRL-B-15,468 and NRRL-B-15,469.

15. The bacterial composition which comprises in admixture:

(a) a nisin producing Streptococcus containing foreign plasmid DNA from a 29 Mdal plasmid encoding for sucrose utilization and nisin production in a Streptococcus which is sensitive to nisin and does not naturally produce nisin; and (b) a nisin resistant *Streptococcus diacetilactis* which produces an inhibitory substance for Gram-negative bacteria, wherein the mixture of the bacteria in the composition produces the inhibitory substance and nisin.

16. The composition of claim 15 containing at least $10^6$ cells per ml as a frozen, dried or lyophilized live culture as a preserved form for storage and shipment prior to use.

17. The composition of claim 15 containing at least $10^9$ cells per ml in a preserved form for storage prior to use.

18. The composition of claim 15 wherein the *Streptococcus lactis* subsp. *diacetilactis* is naturally resistant to nisin.

* * * * *

UNITED STATES PATENT AND TRADEMARK OFFICE
CERTIFICATE OF CORRECTION

PATENT NO. : 4,716,115
DATED : December 29, 1987
INVENTOR(S) : Carlos F. Gonzalez and Alfred J. Gryczka It is certified that error appears in the above-identified patent and that said Letters Patent are hereby corrected as shown below:

```
The following U.S. patents should be cited:
2,935,503   5/3/60      Hawley et al
3,093,551   6/11/63     Hall, R. H.
2,785,108   3/12/56     Hawley, H. B.
3,295,989   1/3/67      Matz, et al
4,237,224   12/2/80     Cohen et al
4,374,200   2/15/83     Olsen
2,744,827   5/8/56      Mattick et al
```

Column 2, line 24 "3) 546-540" should be --3) 546-550--.

Column 3, line 64 "Debaryomuces" should be --Debaryomyces--.

Column 4, line 15 "dusing" should be --using--.

Column 12, line 19 "807 813" should be --807-813--.

Signed and Sealed this

Seventh Day of June, 1988

*Attest:*

DONALD J. QUIGG

*Attesting Officer*    *Commissioner of Patents and Trademarks*